United States Patent
Mansfield et al.

(10) Patent No.: US 7,754,490 B2
(45) Date of Patent: Jul. 13, 2010

(54) MICROFLUIDIC PRECONDITIONING OF (BIO)FLUIDS FOR REAGENT-FREE INFRARED CLINICAL ANALYSIS AND DIAGNOSTICS

(76) Inventors: Colin Mansfield, 12 Beaconfield Close, Sjobury, Suffolk C010 1TR (GB); Anthony Shaw, 337 Queenston St., Winnipeg, Manitoba (CA) R3N 0W9

( * ) Notice: Subject to any disclaimer, the term of this patent is extended or adjusted under 35 U.S.C. 154(b) by 93 days.

(21) Appl. No.: 11/568,937

(22) PCT Filed: May 5, 2005

(86) PCT No.: PCT/CA2005/000687

§ 371 (c)(1),
(2), (4) Date: Mar. 22, 2007

(87) PCT Pub. No.: WO2005/108958

PCT Pub. Date: Nov. 17, 2005

(65) Prior Publication Data

US 2007/0215809 A1    Sep. 20, 2007

Related U.S. Application Data

(60) Provisional application No. 60/569,266, filed on May 10, 2004.

(51) Int. Cl.
*G01N 21/35* (2006.01)
*G01N 21/17* (2006.01)
*G01N 21/00* (2006.01)

(52) U.S. Cl. ............... 436/86; 250/339.12; 250/339.06; 250/339.01; 250/338.1; 250/336.1

(58) Field of Classification Search ................... 436/86; 210/634; 250/339.12, 339.06, 339.01, 338.1, 250/336.1
See application file for complete search history.

(56) References Cited

U.S. PATENT DOCUMENTS 6,454,945 B1   9/2002   Weigl et al.

OTHER PUBLICATIONS

Shaw, R. Anthony et al., Toward Reagent-free Clinical Analysis: Quantification of Urine Urea, Creatinine and Total Protein from the Mid-Infrared Spectra of Dried Urine Films, 2000, 46, No. 9, 1493-1495.*
Houska M. et al., Protein-Suface Interactions Studied by Infrared Spectroscopy, Makromol. Chem., Suppl., 1985, 9, 103-111.*
Weigl B. et al., Lab-on-a-chip for drug development, Advanced Drug Delivery, 2003, 55, 349-377.*
Holl M.R. et al; Optimal Design of a Microfabricated Diffusion Based Extraction System, Proceedings of 1996 ASME Meeting ASME DSC59, pp. 189-195, Aug. 18-25, 1996.
Hawkins, KR et al Diffusion immunoassay for protein analytes, 2nd Annual International IEEE-EMBS Special Topic Conference on Microtechnologies in Medicine & Biology pp. 535-540 May 2-4, 2002 Madison Wisconsin USA.

* cited by examiner

*Primary Examiner*—Walter D Griffin
*Assistant Examiner*—Christine T Mui
(74) *Attorney, Agent, or Firm*—Michael R. Williams; Ade & Company Inc.

(57) ABSTRACT

A number of reagent-free infrared spectroscopic diagnostic and analytical methods have been established previously, making use of dry biofluid films. For example, this approach has successfully measured high concentration analytes of serum and urine. However, a number of low concentration diagnostically relevant analytes presently elude detection by infrared spectroscopy. This is due in part to their relatively low concentration and in part to spectral interference by other strongly absorbing constituents. The applicability of the technique would be broadened substantially if it were possible to separate and concentrate, lower concentration analytes, e.g. serum creatinine and urine proteins, from the obscuring presence of relatively high concentration compounds. The invention disclosed achieves this is through microfluidic sample preconditioning based upon laminar fluid diffusion interfaces. Preferential separation of certain low concentration serum and urine analytes of clinical interest that presently lie just below the threshold of detection by infrared spectroscopy is provided.

10 Claims, 8 Drawing Sheets

MICROFLUIDIC PRECONDITIONING OF (BIO)FLUIDS FOR REAGENT-FREE INFRARED CLINICAL ANALYSIS AND DIAGNOSTICS

PRIOR APPLICATION INFORMATION

This application claims the benefit of U.S. Provisional Application 60/569,266, filed May 10, 2004.

BACKGROUND OF THE INVENTION

In the clinical laboratory today, the majority of serum, blood and urine assays are performed using techniques that employ analyte specific reagents to produce color reactions. These tests play a critical role in diagnosing and monitoring a wide variety of disorders with a hospital typically running many thousands of such assays every month.

Reagent-free infrared (IR) spectroscopic analysis of dried films is a technique that enables the accurate and cost-effective analytical testing of key serum, blood and urine assays, as well as for certain other niche applications [1-11]. This method offers several potential benefits over standard analytical methods: no purchase or storage of reagents is required; several analyte levels may be determined simultaneously from a single spectrum; the technique is non-destructive allowing additional measurements if required; linearity is routinely available over the full range of analyte levels; the use of dried films allows for simple shipment of samples; the method lends itself readily to automation and high volume repetitive measurements; and minimal technical expertise is required of the operator. The method has successfully measured several key serum and urine analytes with accuracy sufficient for routine clinical analysis A key characteristic of this approach is that it eliminates the difficulties associated with strong water absorptions, quantification of analyte levels or diagnoses being most effectively determined via multivariate analysis [1,2], (although any data analysis techniques that extract quantitative or qualitative information from IR spectra are equally applicable). The procedure used to derive a new IR-based analytical method begins by acquiring spectra for a set of samples (typically 200-300), together with the corresponding quantitative analyses for the components of interest (as provided by established analytical methods). The samples are then divided into a training set comprising approximately two thirds of the available samples and a test set made up of the remaining third of the samples. For each analyte of interest, a quantification algorithm is derived via a regression analysis routine, typically using a partial least-squares approach that requires the set of training spectra and corresponding analytical levels as input. As a final gauge of its accuracy, the newly derived algorithm is used to predict analyte levels for the set of test samples. The predicted analyte levels are then compared to their true values. The approach used to develop a new IR-based diagnostic classification test parallels that used to develop analytical methods. First, the spectra for a large number of samples are accumulated for each of the disease categories of interest. Pattern identification software is then used to discover an algorithm that optimally distinguishes disease from control spectra. The classification algorithm is used to predict diagnoses based upon the spectra for an independent set of test samples and the predicted diagnoses compared to true diagnoses.

A number of diagnostically relevant analytes presently elude detection by IR spectroscopy due to insignificant contributions to the overall IR profile. This is due in part to their relatively low concentration and in part to coincidence of their absorption bands with those of other strongly absorbing constituents. Since all IR absorbing compounds contribute absorption patterns that are superimposed onto one another, the measured absorption profile is typically dominated by a small number of the most concentrated analytes. This imposes a constraint on how much material may be dried to provide a useful IR spectrum; beyond a certain limit, absorption by the predominant compounds completely blocks incident IR light, effectively impeding spectroscopic determination of analytes below a certain concentration threshold. This in turn places a clear lower limit on the concentration range of analytes that may be determined by IR spectroscopy of multi-constituent samples. However, lower concentration analytes would be accessible simply by drying a greater amount of the (bio)fluid under investigation (longer effective optical pathlength) if the dominant constituent's influence were to be considerably reduced or removed.

A microfluidic sample preconditioning technique, often referred to as laminar fluid diffusion interface (LFDI) [12-26], provides the basis to accurately quantify analytes that are otherwise inaccessible to reagent-free IR spectroscopy, while preserving all of the advantages of reagent free spectroscopy as discussed above.

SUMMARY OF THE INVENTION

The invention described here I) expands the range of analytes that may be determined quantitatively by infrared spectroscopy of complex mixtures, and II) demonstrates utility for the invention in the analysis of clinical specimens such as urine and serum. As such, the invention addresses limitations and drawbacks both inherent to the present state-of-the-art in clinical analysis and to the IR spectroscopic analysis of biofluids. These are addressed separately as I) and II) below. (As used herein, the term "biofluid" refers to any multi-constituent fluid sample, native or derived, that contain analytes of varying molecular weights. Samples applicable to LFDI preconditioning for reagent-free IR clinical analysis and diagnostics include, but are not restricted to, bodily fluids (e.g. serum, urine, whole blood), biological matter dissolved and/or suspended in a fluid matrix (e.g. supernatant from homogenized stool samples), fluid samples (native or derived) pertaining to the biosphere, industrial production, or effluents).

I. Clinical laboratories at present rely upon central instrumentation to carry out the vast majority of serum and urine tests. This instrumentation carries out the majority of required chemical analyses by setting up chemical reactions, making use of specific chemical reagents as the basis to recognize and quantify individual components in these complex specimens. By its nature, therefore, the clinical laboratory relies upon a steady supply of high quality reagents, and must store those reagents prior to use. The costs of purchasing reagents is high enough that reagent suppliers typically provide instrumentation "free" with the stipulation that the user contracts to purchase reagents from that supplier. Reagent cost is therefore a drawback inherent to this approach to analysis. A second limitation is that reagents typically require refrigeration during transport and storage-requirements that make reagent-based testing impossible in certain parts of the developing world. The required storage conditions for reagent-based analysis therefore represent a second drawback to this approach.

II. The drawback to infrared spectroscopic analysis as presently practised is that there are limits to the range of analytes that may be determined quantitatively for complex mixtures.

In particular, the absorption features of low concentration analytes are masked by those of high concentration analytes; while in principal the absorptions of interest for the less abundant compound may be brought into prominence by using a longer optical pathlength, this is not a practical solution for complex mixtures. Above a certain threshold, the more abundant species completely absorb the incident light, and it becomes impossible to collect meaningful spectra. This represents the fundamental limitation of IR spectroscopy of mixtures as a basis for separate quantification of the mixture's individual components.

According to the invention, the applicability of the IR analysis technique has been broadened substantially by sample pre-conditioning, including separating and concentrating, low concentration analytes prior to their IR spectroscopic analysis. More specifically, pre-conditioning of samples by microfluidic laminar fluid diffusion interface (LFDI) is provided. In particular, LFDI provides a basis to enhance the relative concentration of certain analytes in a manner that preserves the advantages that reagent-free IR clinical diagnostics has over present day classical laboratory analytical methods. Dried films of enhanced effective concentration (the product of analyte concentration and pathlength) can then be prepared and IR spectroscopic analysis used to quantify analytes that would otherwise be impossible to quantify by IR. For example, diagnostically relevant analytes that become accessible include serum creatinine and urine protein. In serum, low concentration creatinine (molecular weight approx. 132 Da) is separated from the comparatively high molecular weight (approx. 68,000 Da) and high concentration serum proteins, while for urine, low concentrations of urine protein are separated from the comparatively low molecular weight (approx. 60 Da) and high concentration, urea. The relative concentrations of relevant urine and serum analytes would thereby be increased sufficiently to render them detectable by IR spectroscopy. The same sample preconditioning described here for use in quantitative clinical analytical tests is equally pertinent to disease classification IR diagnosis[8-11]. Here, rather than deriving analyte levels from IR spectrum, subtle spectral patterns are used to distinguish normal specimens from those corresponding to diseased patients.

In other embodiments, pre-conditioning of the sample may be used to separate serum albumin from serum samples, thereby allowing analysis of serum's other spectroscopic analytes. In yet other embodiments, preconditioning of a urine sample is used to separate urea and/or creatinine from analytes of interest in urine.

LFDI sample preconditioning of samples for reagent-free IR clinical analysis and diagnosis provides (1) detection of low (trace) concentration analytes, therefore broadening the range of analytes accessible to IR clinical spectroscopy; (2) a sharper 'probe' to optimize diagnostic methods based upon pattern recognition; (3) an alternative to the centrifugation process, which is highly advantageous when considering developing point-of-care IR spectroscopic diagnostics; and (4) a robust, flexible and cost effective technological platform (e.g. polydimethylsiloxane fabricated cards).

According to a first aspect of the invention, there is provided a method of analyzing a liquid sample comprising:

(a) flowing a liquid sample as a first stream through a microfluidic laminar fluid diffusion interface device while simultaneously flowing a second stream of a receiver liquid through said device such that diffusion occurs between the first stream and the second stream;

(b) collecting the first stream and the second stream from the device; and (c) subjecting the first stream or the second stream to infrared spectroscopic analysis.

According to a second aspect of the invention, there is provided a method of analyzing a liquid sample comprising:

(a) providing a liquid sample wherein the infra-red spectroscopic signal of a first analyte of interest is dominated by the infrared spectroscopic signal of a second analyte, said first analyte and said second analyte having different diffusion coefficients;

(b) flowing the liquid sample as a first stream through a microfluidic laminar fluid diffusion interface device while simultaneously flowing a second stream of a receiver liquid through said device such that diffusion occurs between the first stream and the second stream, thereby concentrating the analyte of interest relative to the second analyte;

(c) collecting the first stream and the second stream from the device; and (d) subjecting the stream containing the analyte of interest to infrared spectroscopic analysis.

DETAILED DESCRIPTION OF THE INVENTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method of analyzing a liquid sample, for example, a biofluid as described herein, comprising:

(a) providing a liquid sample wherein the infra-red spectroscopic signal of a first analyte of interest is dominated by the infrared spectroscopic signal of a second analyte, said first analyte and said second analyte having different diffusion coefficients;

(b) flowing the liquid sample as a first stream through a microfluidic laminar fluid diffusion interface device while simultaneously flowing a second stream of a receiver liquid through said device such that diffusion occurs between the first stream and the second stream, thereby concentrating the analyte of interest relative to the second analyte; and (c) collecting the first stream and the second stream from the device; and (d) subjecting the stream containing the analyte of interest to infrared spectroscopic analysis.

In other embodiments, there is provided a method of analyzing a liquid sample comprising:

(a) flowing a liquid sample as a first stream through a microfluidic laminar fluid diffusion interface device while simultaneously flowing a second stream of a receiver liquid through said device such that diffusion occurs between the first stream and the second stream;

(b) collecting the first stream and the second stream from the device; and (c) subjecting the first stream or the second stream to infrared spectroscopic analysis.

That is, in these embodiments, a molecular weight biased (analyte enhanced) spectrum is prepared by preferentially separating the sample into two separate streams based on diffusion coefficient. As discussed above, all IR absorbing compounds contribute absorption patterns that are superimposed on one another. Thus subjecting a complex sample to LFDI separates high and low diffusion coefficient components and thereby alters the relative concentrations of high and low molecular weight analytes, producing a high MW spectra and a low MW spectra. In some embodiments, the spectrum or spectra are then subjected to spectral pattern recognition analysis as discussed below.

As discussed below, the first stream and/or the second stream may be re-applied to the microfluidic laminar fluid diffusion interface device or to a new microfluidic laminar fluid diffusion interface device following the initial separation.

Microfluidics are emerging as one of the fastest growing segments of microtechnology, with an established literature and commercial base. One application of particular relevance is the separation of sample components based upon differences in their diffusion coefficients (which in turn are closely related to their molecular weight). The magnitude of the diffusion coefficient depends on the diffusing molecule and on the medium in which it is diffusing. The diffusion coefficient is a function of the absolute solvent viscosity, $\eta$, temperature, T, Boltzman's constant, k, and characteristic size of the particle, a. It is expressed as the Einstein relation $$D = \frac{kT}{6\pi\eta a}$$

The mean distance, I, a particle diffuses in time, t, is given by the relation $$l = \sqrt{2Dt}$$

Thus, large particles have smaller diffusion coefficients and diffuse a shorter distance in a given amount of time than smaller particles.

The separation occurs when two individual streams flow in parallel through a single microfluidic channel, the scale of which ensures laminar flow. Fluid flow is typically characterized as either laminar or turbulent; the specific regime of a fluid flowing in a channel being determined by the ratio of inertial to viscous forces and described by the Reynolds number. Laminar flow is dominated by viscous forces, (i.e. low Reynolds number), in which fluid streams flow parallel to each other and mix only through convective and molecular diffusion. Convective mass transport only occurs in the direction of fluid flow. Hence, while there is no turbulent mixing, chemical exchange from one stream to the other does occur via diffusion. This technique, for which no macroscopic equivalent exists, is often referred to as laminar fluid diffusion interfaces (LFDI) [12-26]. Typically, one stream is the sample under investigation (in the present case, a biofluid with constituents varying widely in molecular weight), whilst the second stream is a neutral receiver fluid such as filtered water. Other suitable receiver fluids for IR reagent-free analysis include for example but are by no means limited to Phosphate Buffer Solution (PBS) for samples that possess cellular contents (e.g. whole blood), and filtered water containing a simple internal standard (e.g. KSCN). In some embodiments, receiver fluids that possess an affinity to a given analyte may also be employed to enhance the natural diffusive separation phenomenon. Upon exiting the diffusion channel the fluid can once again be cleanly split into two separate output streams, designated here as the "receiver" and "sample" stream outputs that are enriched and depleted, respectively, in constituents of low molecular weight. If the target analyte is of low molecular weight compared to the dominant absorbing compound, e.g. in the separation of serum creatinine from highly concentrated protein, then the analyte of interest (creatinine) would be preferentially extracted from the sample stream and quantified via IR spectroscopy of the receiver stream. If the target analyte possesses a high molecular weight relative to the dominant absorbing compound, as is the case for urine protein (urea absorptions dominate the IR spectrum of urine), then the relative concentration of the analyte of interest (protein) increases in the sample stream as the low molecular weight constituents diffuse rapidly to the receiver stream. Dried films from the serum receiver stream output and the urine sample stream output are then analyzed to accurately quantify serum creatinine and urine protein respectively; as discussed above, these analytes are otherwise inaccessible.

In general, any analytes that differ in molecular weight (MW), and therefore diffusivity, will exhibit a preferential separation following their transit through a LFDI-diffusion channel. The extent of this separation, (i.e. the change in relative concentrations achieved), depends upon the relative magnitude of their MW disparity, operational and physical parameters of the LFDI-card (e.g. diffusion channel length, residency time in the diffusion channel, stream flow rates and height of the virtual diffusion barrier thus defined), and the degree of dilution that can be tolerated or compensated for, (i.e. volume of LFDI-processed sample deposited into a dry film). Separation is most effective when extracting a low molecular weight analyte (say, MW<1000 Da) from a high molecular weight analyte (say, MW>60000 Da) or cellular material. Mathematical simulations of the diffusion process (based upon Einstein's Relation) show that if targeting low MW analytes a change in relative concentration of $10^3$-fold is quite feasible, albeit with a significant degree of dilution. This factor is smaller when targeting high MW analytes but dilution is much less significant. The key parameter in separating dissolved species from one another is the relative difference rather than the absolute difference in molecular weights; when molecular weights are similar a greater separation will occur for low MW analytes, (e.g. urea (MW~60 Da) and creatinine (MW~132 Da)), than would be observed in higher MW analytes of the same absolute difference.

The aim of the experiments reported here was to verify that LFDI separation can indeed alter the relative concentrations of relevant urine and serum analytes by a degree sufficient to render their IR spectral contribution as meaningful.

Materials and Methods

Materials

Microfluidic 'passive' LFDI-cards (H-Card GVH-9026A) were purchased from Micronics Inc. (Redwood, Wash., USA). Product applications for these cards are reported to include: PCR product clean up; separator, reactor and extractor for bio-pharmaceutical and drug discovery applications; separator for process control and environmental applications; microreactor for preparative synthetic chemistry; artificial kidney; genomic analysis systems, sequencers; DNA desalting, and extraction of small proteins from whole blood samples. The overall dimensions of these cards are similar to those of a credit card. Two input reservoirs are positioned at the top of the card for the receiver and sample fluids. These fluids are drawn into the microchannels via capillary action and upon inversion of the card into a vertical position flow is driven passively by hydrostatic pressure. The streams converge and merge to flow in parallel, thereby establishing the LFDI in a single diffusion channel. At the diffusion channel exit the flow is split into two separate streams again and collected into reservoirs at the bottom of the card. These passive LFDI-cards allow for continuous separation, by periodically replenishing and emptying the appropriate reservoirs.

The target analytes were serum creatinine and urine protein since these are analytes of clinical interest that presently lie just below the threshold of detection by IR spectroscopy due to the masking of their respective signals by other components, as discussed herein. Other IR reagent-free applications that LFDI preconditioning is anticipated to be advantageous to include, but are not restricted to, dialysis monitoring (spectral enhancement of creatinine and urea concentrations from whole blood), lipid profiling including direct LDL, HDL, Apo B, Apo A1 (spectral enhancement of these serum analytes following extraction of albumin and lower MW analytes), colon cancer (via stool supernatant spectral pattern recognition across a range of molecular weight enhancements), fetal lung maturity (spectral enhancement of amniotic fluid's lipid components (lecithin/sphingomyelin) following extraction of albumin and lower MW analytes), and acute cardiac markers (via serum or whole blood spectral pattern recognition across a range of molecular weight enhancements).

To facilitate visual tracking of the relevant spectroscopic trends (as opposed to the barely perceptible influences at or near normal physiological levels), simulated serum and urine solutions were prepared with abnormally high creatinine and protein concentrations respectively, to model the enrichment processes (the normal adult reference interval for serum creatinine is 53-115 µmol $L^{-1}$, and for urine protein is 10-140 mg $L^{-1}$) [27]. Pig serum and urine samples were spiked with creatinine and albumin respectively, targeting lower final creatinine and albumin concentrations to simulate more realistic conditions within the complex matrix of genuine samples.

Filtered water drawn from a laboratory reverse osmosis purification unit was used to prepare simulated "serum" and "urine" specimens, and also served as the receiver fluid. The simulated serum and urine samples were aqueous solution including the major soluble IR absorbing constituents, prepared using chemicals from Sigma (St. Louis, Mo., USA), with substantially elevated serum creatinine and urine protein levels. Simulated serum included albumin (12.5 g $L^{-1}$), glucose (5 mmol $L^{-1}$), urea (5 mmol $L^{-1}$) and the target analyte creatinine (6 mmol $L^{-1}$) mixed in aqueous potassium thiocyanate (KSCN) at 2 g $L^{-1}$. Simulated urine included urea (240 mmol $L^{-1}$), creatinine (8 mmol $L^{-1}$), glucose (1.6 mmol $L^{-1}$) and the target analyte albumin (8 g $L^{-1}$) mixed in aqueous KSCN (4 g $L^{-1}$).

For the present study, KSCN was added to the various samples to act as an optical tracer, to track the redistribution of low molecular weight compounds (i.e. those with molecular weights and hence diffusion coefficients similar to those for $SCN^-$) following passage through the LFDI-card. KSCN has been exploited previously as an internal standard for the compensation of sample deposition volume (i.e. optical pathlength) variations via spectral normalization [5,6]. Various compounds other than KSCN could feasibly be used for this purpose provided they possess a unique absorption peak within the spectral window of approximately, 2000-2600 $cm^{-1}$, (e.g. ferricynanide, thiocynates, isocynates, azides), however, KSCN is favored since its associated C≡N stretching mode provides an isolated absorption band at approximately 2060 $cm^{-1}$, it is of no detriment to the sample, relatively benign, inexpensive, stable, and easy to handle. The inclusion of an internal standard for transmission or reflectance spectral acquisition is prudent where manual film deposition is practiced but would become a redundant measure for automated deposition techniques of inherently good precision (e.g. high throughput sampling or lab-on-chip).

Genuine serum and urine specimens were collected from pigs in accordance with a protocol approved by the Institute for Biodiagnostics, National Research Council Canada. Whole blood specimens were collected in vacutainers containing the anti-clotting agent EDTA and centrifuged. The serum fraction was then diluted four-fold with aqueous KSCN (2 g $L^{-1}$) and spiked to a creatinine concentration of 1 mmol $L^{-1}$ (approximately 10 times typical physiological levels). The urine sample was mixed in aqueous KSCN (4 g $L^{-1}$) to a ratio of 5:1, and then spiked to an albumin concentration of 800 mg $L^{-1}$ (approximately 10 times typical physiological levels).

Sample Preconditioning and Film Creation

The receiver fluid and sample were warmed to slightly above room temperature to out-gas them prior to their introduction to the LFDI-card. This degassing step is necessary to avoid the release of dissolved gases that may occur as the fluid's temperature, rises. The presence of trapped air in the LFDI-card's channels, or associated pump system for pressure driven cards, can provide an unacceptable amount of capacitance, affecting the separation process.

For the purpose of this study, to surmount limitations of the passive LFDI cards, multiple passages of the relevant output stream were performed to enhance the desired effect. For example, the urine sample stream output (with enhanced protein relative concentration) was passed through a second LFDI-card, anticipating further relative enrichment in protein through further depletion of the lower molecular weight constituents. The process was repeated if necessary, as discussed below. Ideally, the desired analyte concentration manipulation would be produced within a single LFDI-diffusion channel. Ideally, the desired analyte concentration manipulation would be produced within a single LFDI-diffusion channel. This goal is attainable through the use of pressure driven 'active' LFDI-card technology, which provides control over the LFDI-diffusion channel's operational parameters, and customized IR-specific LFDI-card, (i.e. designed for adequate sample volume throughput to permit film deposition of longer optical pathlength). However, the use of sequential passages through LFDI-diffusion channels is useful to enhance the change in relative analyte concentrations for samples where this value is relatively small following a single pass, (e.g. in the separation of relatively low molecular weight analytes from a targeted high molecular weight analyte, the separation of analytes possessing small differences between their diffusion coefficients, and where a mid-molecular weight analyte needs to be separated from both relatively high and low molecular analytes).

The processed streams of interest were dried to films by evenly spreading small volumes onto an appropriately dimensioned IR compatible substrate, (e.g. calcium fluoride, silicon, germanium, sapphire, zinc sulphide, zinc selenide, thallium bromo-iodide etc), and then thoroughly dried, (for this study circular barium fluoride ($BaF_2$) windows of diameter 13 mm and thickness 2 mm were used, with drying conducted under moderate vacuum). Duplicate films were prepared depositing 10 μl and 12 μl of the original serum and urine specimens respectively, and between 40 μl and 400 μl of the sample and receiver stream outputs (one stream being relatively enriched in the sample's abundant analyte(s) but somewhat diluted from the original sample, while the other stream is relatively enriched in the sample's low concentration analyte(s) and has also experienced dilution). Limitations on the volume of aqueous sample that can be placed freely onto a window of this area meant that films of greater sample volume than 40 μl were built up through sequential sample deposition and drying steps, effectively "stacking" one film on top of the other.

Infrared Spectra

IR absorption spectra encompassing the spectral range of 700 to 4000 $cm^{-1}$ were acquired for each dry film using a custom manufactured multisampler, mounted into the sample compartment of a Bruker Vector 22 HTS-XT Fourier transform IR spectrometer, with a blank $BaF_2$ window used for the background measurement. The spectrometer was purged for at least 15 minutes with dry air to remove atmospheric water vapour and $CO_2$ and a total of 256 and 64 scans acquired at 4 $cm^{-1}$ resolution for the background and sample spectra respectively. Comparative analysis of spectral profiles was conducted after performing common spectral manipulations such as baseline, offset corrections and ordinate auto scaling, using appropriate software packages, (e.g. GRAMS/32 (Galactic Industries, Salem, N.H., US) and MATLAB (The Mathworks Inc., South Natick, Mass.)).

Results and Discussion

The ideal performance from any separation technique would result in full recovery and separation of the target analyte from all other constituents. The practical aim of the present study was not so stringent. In practice, quantification through partial least squares requires only that the absorption profile of the target analyte should impact significantly on the sample's overall IR spectral profile. The present aim, therefore, was to identify features distinguishing the spectra of the preconditioned streams from those of the original sample, and to correlate those with changes in the relative concentration of the target species. Since multivariate analysis exploits subtle spectral signatures that may be spread over a wide spectral range, far subtler changes in relative concentration may lead to accurate quantification or diagnosis. It is interesting to note that the spectral regions of optimal utility in quantifying a particular analyte may not necessarily coincide with the analyte's most prominent absorption bands. For example, an IR-based classification scheme has been developed to distinguish type 1 diabetics, type 2 diabetics, and healthy donors, in which the none of the discriminating spectral regions coincide with major glucose absorptions [10].

Figure 1:
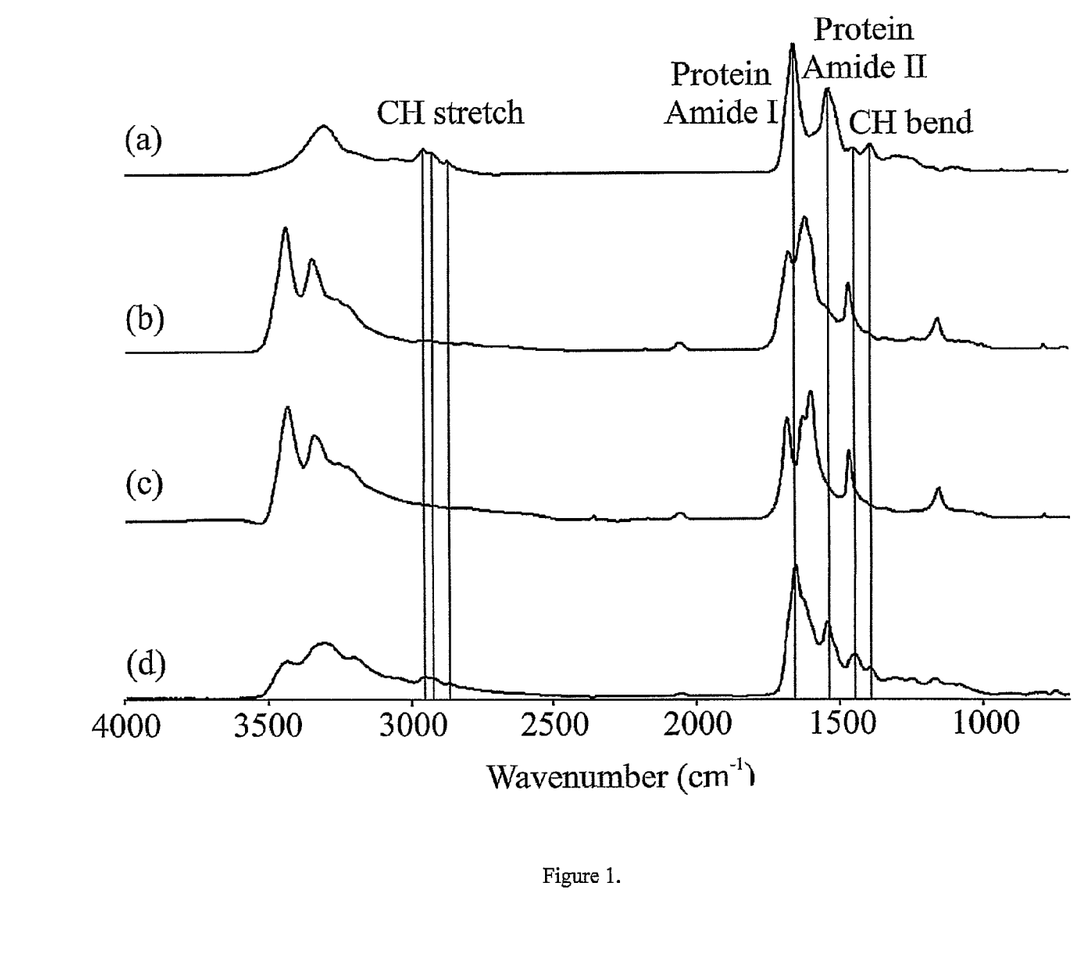
FIG. 1. Infrared absorption spectra of simulated urine spiked to an albumin concentration of approximately 8 g L$^{-1}$; (a) albumin reference solution, (b) original sample (12 µl), (c) single pass receiver stream output (40 µl), and (d) double pass sample stream output (120 µl). Guidelines highlight the correspondence between protein absorptions in the processed urine (d) and pure albumin (a).

The spectra of the receiver and sample streams following LFDI passage of the albumin-spiked simulated urine sample are both very similar to the spectrum of the original sample (FIG. 1). This is to be expected, since urine's IR spectrum is strongly dominated by absorptions of urea, which diffuses rapidly into the receiver stream as a consequence of its low molecular weight. Although a substantial fraction of the urea is transferred to the receiver stream, the relative concentration of heavier constituents (e.g. protein) is not yet sufficient to bring their absorptions into prominence in the spectra of the sample stream. The expected (and desired) enrichment in protein is confirmed, however, by the striking spectral changes that ensue following a second LFDI passage of the initial sample stream output. The dominant absorber within the sample stream output has now become albumin (FIG. 1*a*, 1*d*). A close second examination of the original sample and receiver stream output spectra does reveal the shift in relative concentrations (FIG. 1*b*, 1*c*); absorption features relating to the protein CH stretching and protein amide II regions are clearly weaker in the spectrum of the receiver stream as compared to the original sample.

Figure 2:
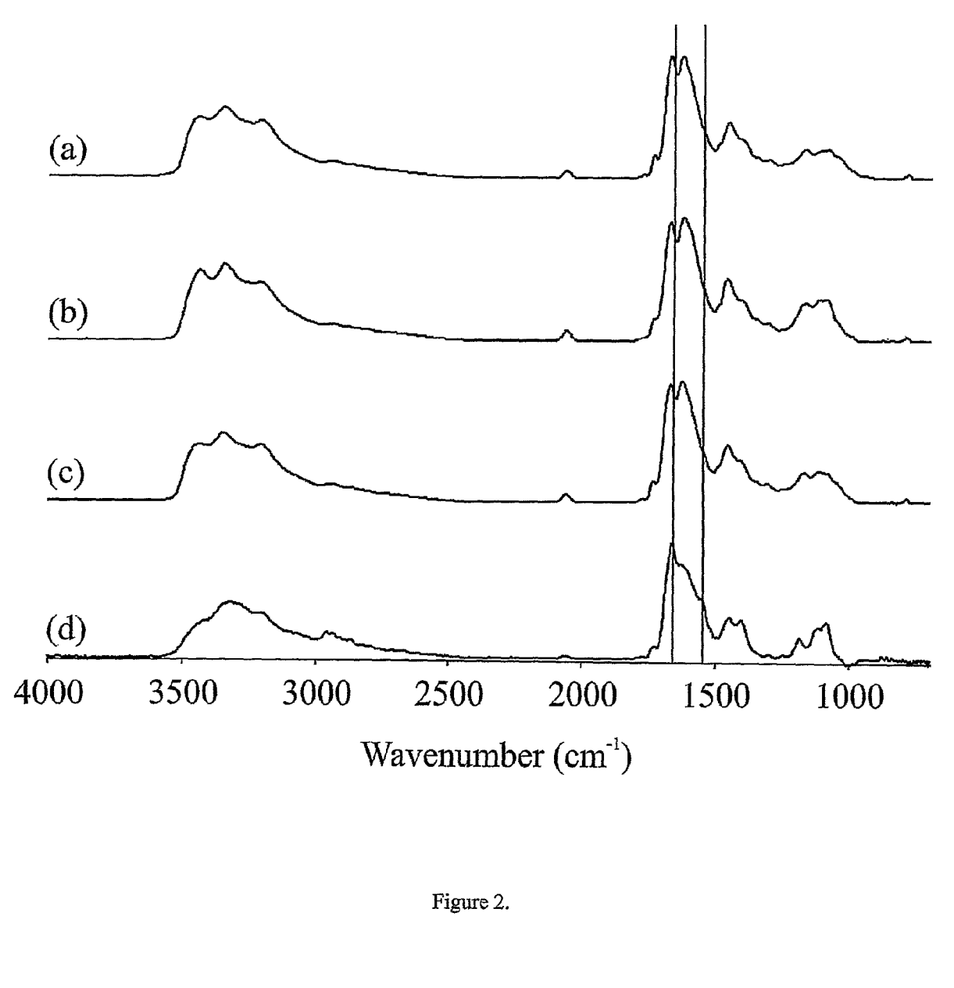
FIG. 2. Infrared absorption spectra of pig urine spiked to an albumin concentration of approximately 800 mg L$^{-1}$; (a) original sample (12 µl), (b) single pass receiver stream output (80 µl), (c) single pass sample stream output (40 µl), and (d) triple pass sample stream output (200 µl). Guidelines indicate the positions of protein amide I and II absorption bands.

The spectra for the genuine pig urine sample (spiked to an albumin concentration of 800 mg $L^{-1}$) show trends parallel to those observed for the simulated urine trials (FIG. 2). Spectra of the original sample, receiver stream output and sample stream output are virtually identical following a single passage through the LFDI-card, and remain similar following a second passage. All are dominated by the IR absorptions of urea. Upon a third passage of the sample stream output however, protein CH stretching, bending, and amide bands become clearly and reproducibly apparent (FIG. 2*d*).

Figure 3:
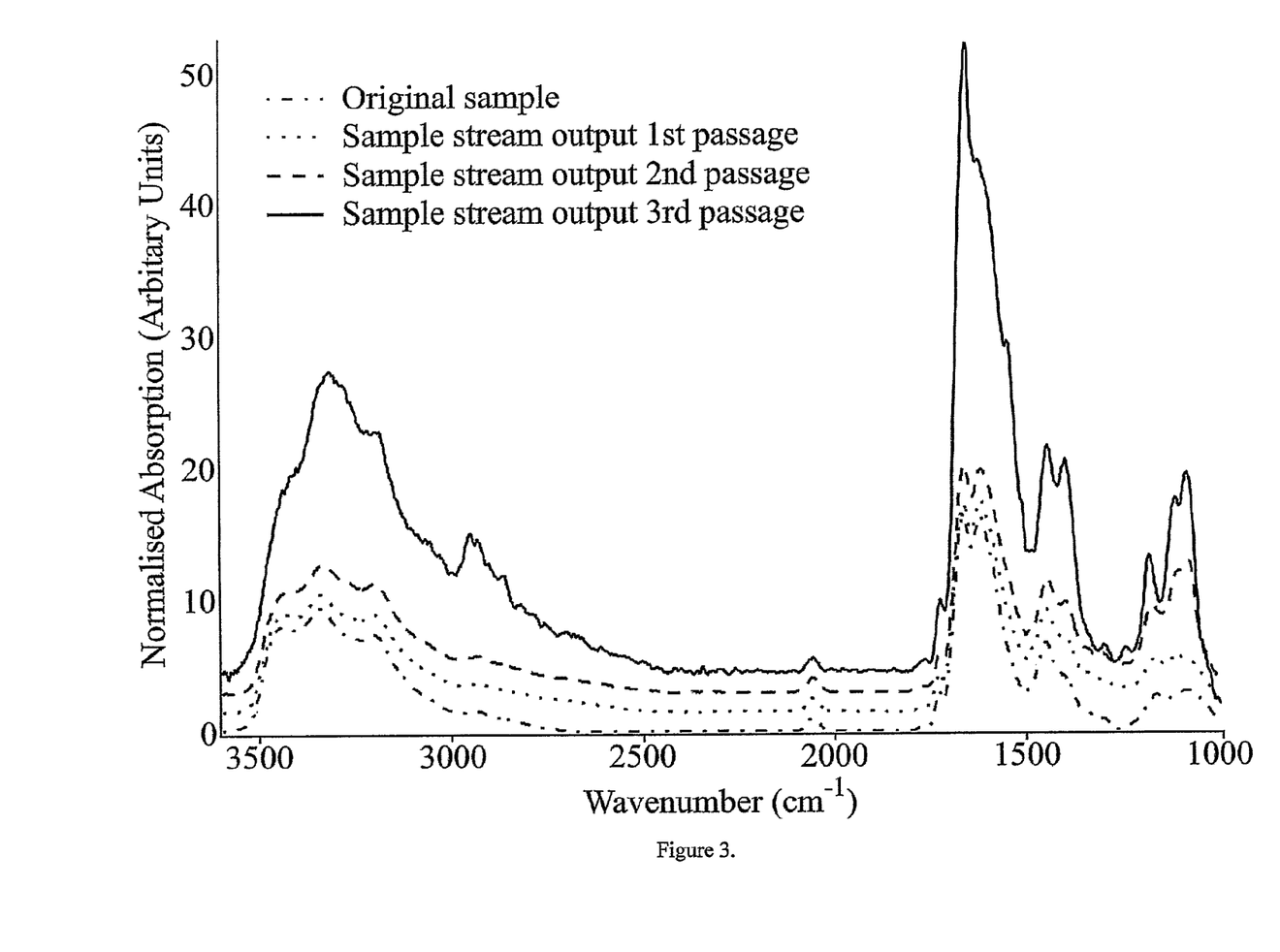
FIG. 3. Infrared absorption spectra of pig urine (spiked to an albumin concentration of approximately 800 mg L$^{-1}$) and LFDI preconditioned streams. Normalization to the KSCN absorption band demonstrates changes in relative concentration amongst the original sample and successive sample stream outputs. Only following a 3$^{rd}$ passage is urea depleted to the extent that protein absorptions (marked with asterisks) appear in the IR spectral profile. The spectra have been offset on the vertical axis for clarity of presentation.

The changing proportion between high and low molecular weight constituents is clearly illustrated by normalizing the spectra to a common KSCN band intensity. KSCN crosses the diffusion boundary in tandem with the low molecular weight sample constituents; because $SCN^-$ and urea possess similar molecular weights (50 and 60 Daltons respectively), both might reasonably be expected to diffuse at comparable rates, so that the KSCN effectively serves as a low molecular weight tracer. The ratio [$SCN^-$]/[urea] in the original sample is therefore expected to be preserved for the sample stream and receiver stream outputs. This expectation is confirmed by normalizing the spectra of the original sample and the three successive LFDI sample streams to a common intensity in the 2060 $cm^{-1}$ absorption of $SCN^-$, as depicted in FIG. 3. The close similarity in the normalized spectra for the original sample and the first two sample streams confirm that urea and $SCN^-$ do indeed cross the diffusion boundary at similar rates. Upon the third passage, urea is depleted to such an extent that absorptions of protein begin to dominate the residual urea (and $SCN^-$) absorptions. The striking emergence of protein absorption bands following multiple LFDI passes, is in accordance with the anticipated theoretical performance of the passive LFDI cards used. Assuming optimal LFDI performance, i.e. full retention of the sample's high molecular weight constituents within the sample stream and concentration equilibrium of its low molecular weight constituents between streams, then the diffusion channel's geometry (9:1 ratio of receiver to sample stream volumes) produces an approximate 10-fold change in the sample stream output's relative concentration. Hence, the first, second and third LFDI passes give rise to 10:1, 100:1 and 1000:1 enhancements in the concentration of the high molecular weight constituents relative to it's the low molecular weight constituents. Also of interest is the emergence of the three absorptions in the 1000-1200 $cm^{-1}$ range. First appearing in the second sample output stream, and more prominently in the third, these are glucose absorptions, presumably increasing in prominence due to the relatively slow diffusion to the receiver stream as compared to KSCN (and urea).

Interpretation of the serum spectra is less clear-cut than for urine. A useful separation (i.e. a separation that might open the door to accurate creatinine quantification) would lead to the creatinine absorption spectrum making a meaningful contribution to the sample's overall IR spectral profile, however an explicit qualitative demonstration of this is improbable, since other constituents of comparable molecular weight, e.g. urea, will experience a similar concentration enhancement relative to protein. This does not preclude its successful quantitative determination, however; although the enhancement of creatinine concentration relative to protein concentration may not explicitly be visually tracked, it may be deduced by tracking changes in the relative concentration of serum's low molecular weight constituents collectively.

Figure 4:
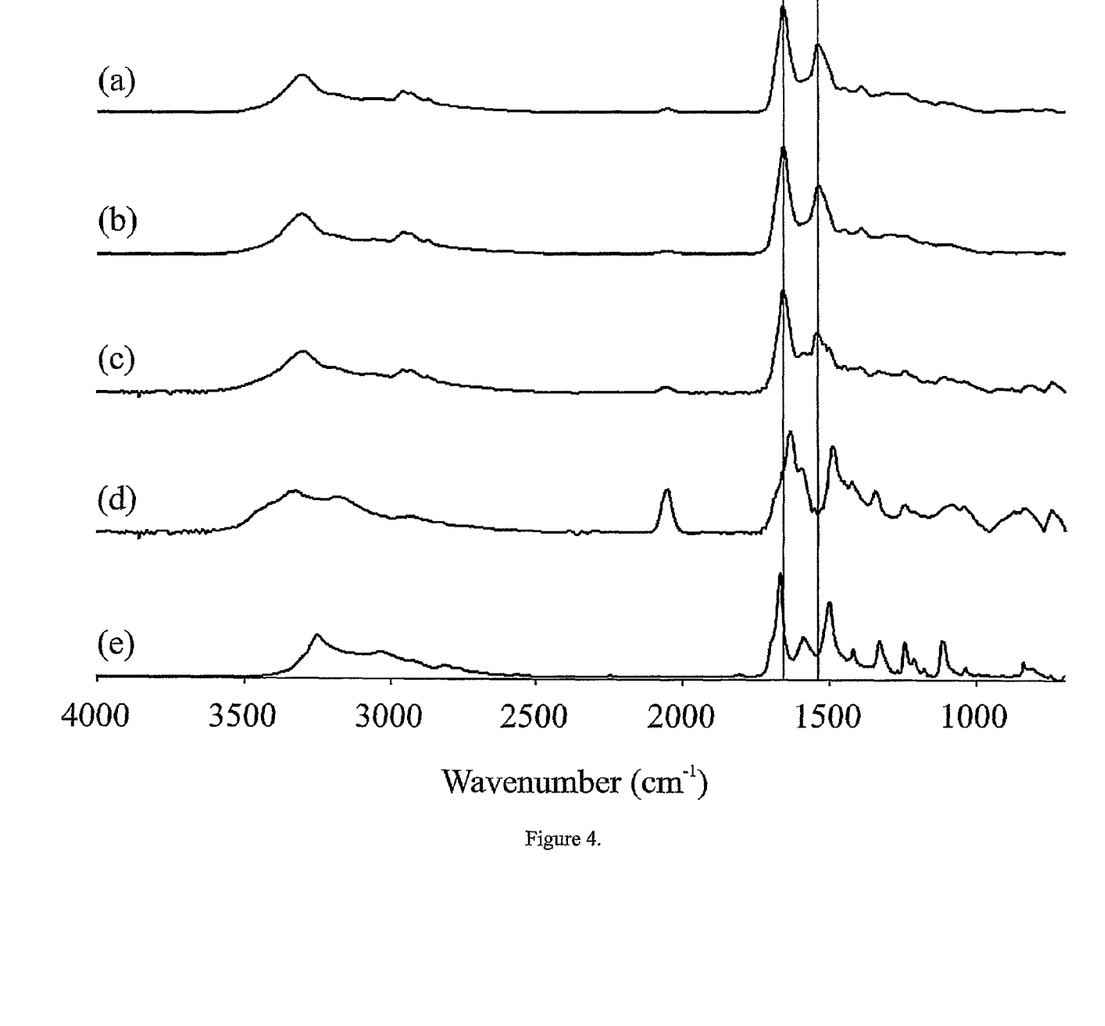
FIG. 4. Infrared absorption spectra of simulated serum spiked to a creatinine concentration of approximately 6 mmol L$^{-1}$; (a) original sample (40 µl), (b) single pass sample stream output (120 µl), (c) single pass receiver stream output (120 µl), (d) double pass receiver stream output (360 µl), and (e) creatinine reference solution. Guidelines indicate the positions of protein amide I and II absorption bands.

The spectra for simulated serum specimens following a single pass through the LFDI-card are shown in FIG. 4. While a single pass through the passive LFDI-card is not sufficient to break protein's dominance over the IR profile of the receiver stream output, significant differences do appear when the single-pass receiver stream output is passed through a second LFDI-card. The protein absorptions in this second receiver stream are reduced to insignificance, so that the low molecular weight constituents (urea, creatinine, and $SCN^-$) now dominate the absorption profile.

Figure 5:
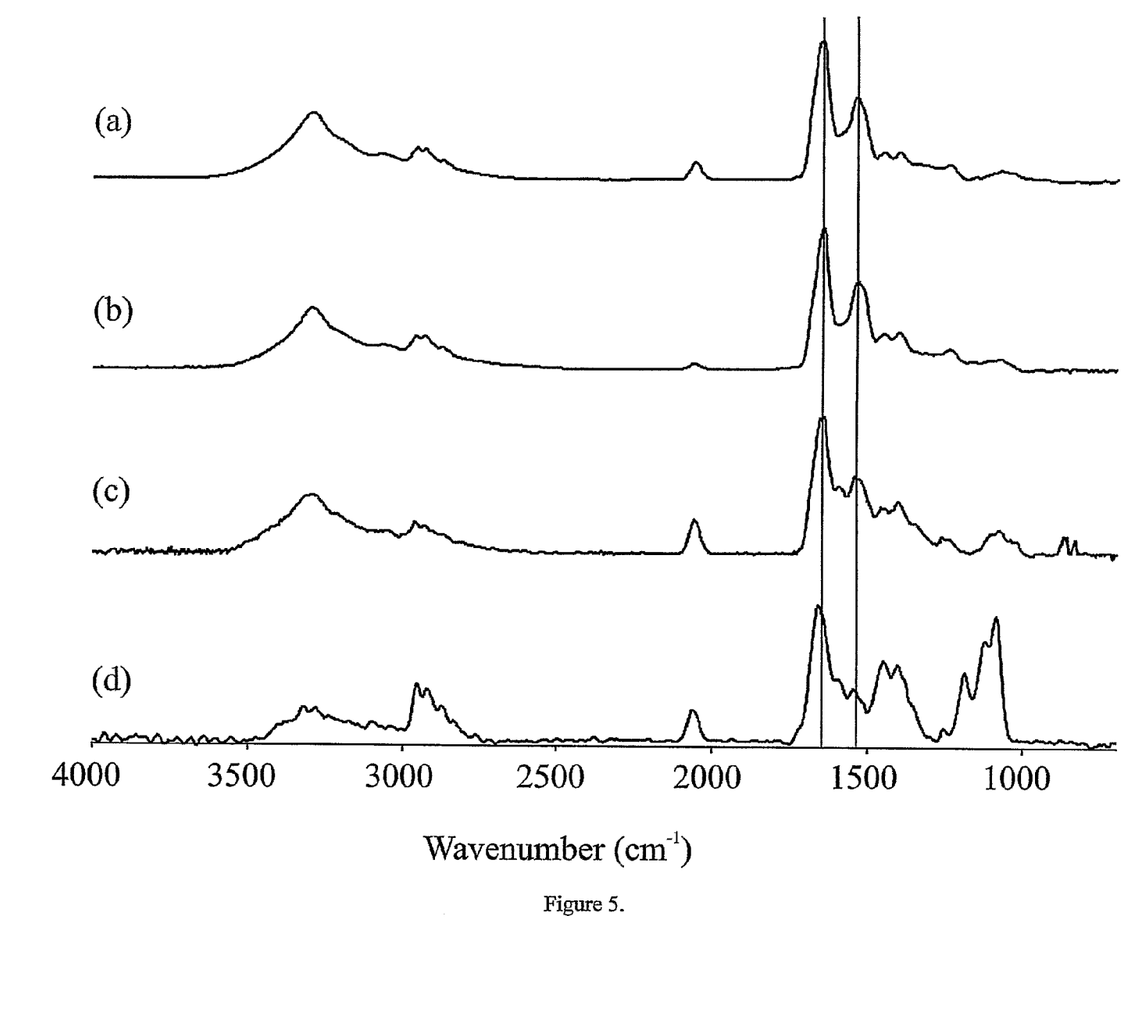
FIG. 5. Infrared absorption spectra of pig serum spiked to a creatinine concentration of approximately 1 mmol L$^{-1}$; (a) original sample (10 µl), (b) single pass sample stream output (80 µl), (c) single pass receiver stream output (80 µl), and (d) double pass receiver stream output (400 µl). Guidelines indicate the positions of protein amide I and II absorption bands.
Figure 6:
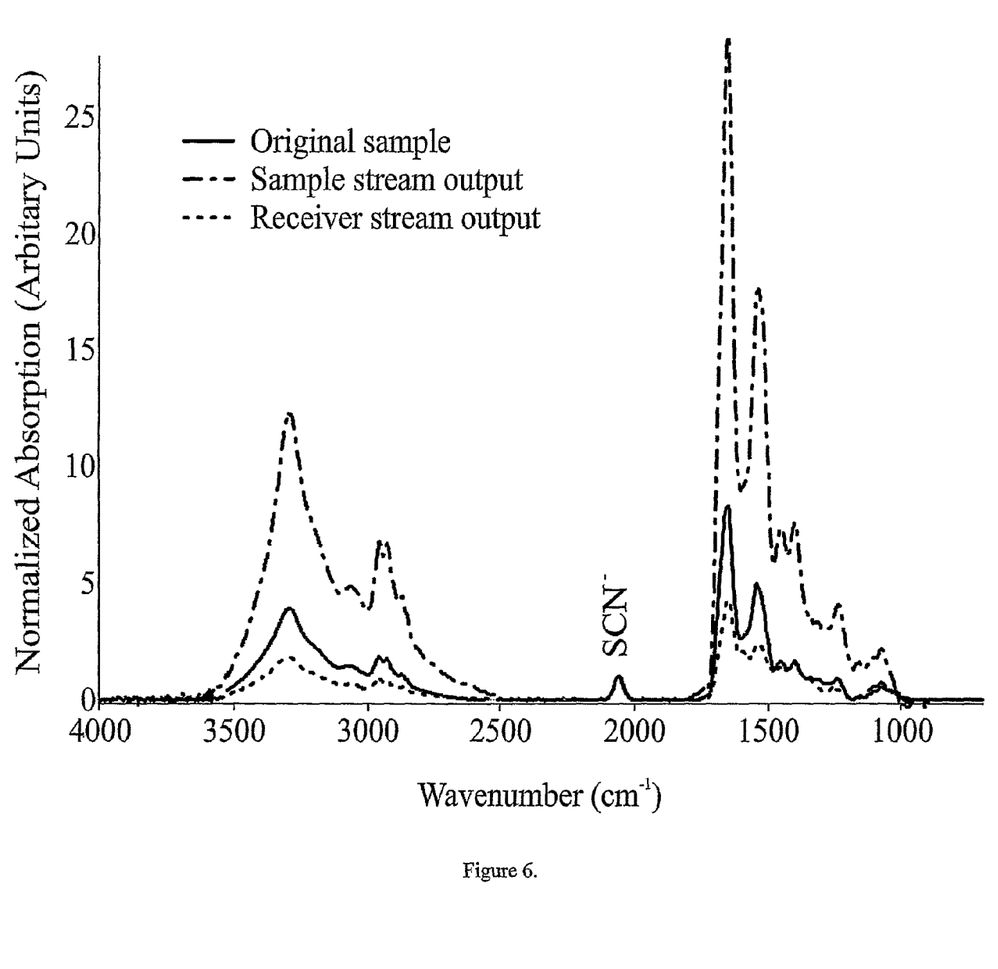
FIG. 6. KSCN-normalized absorption spectra of pig serum spiked to a creatinine concentration of approximately 1 mmol L$^{-1}$ and of the LFDI preconditioned outputs. The relative concentration of protein is enhanced and diminished with respect to the low molecular weight constituents in the sample stream and receiver stream outputs, as compared to the original sample.

In the case of genuine pig serum sample (spiked with creatinine), protein still contributes substantially to the spectrum of the double-passed receiver stream output (FIG. 5d). The desired effect is indicated, nevertheless, by comparing this spectrum to that of either the original sample or the sample stream output (FIG. 5a, 5b). The protein amide II band is diminished in intensity, the CH stretching profile (3000-2800 $cm^{-1}$) is altered, and new absorption features have emerged at approximately 1600 $cm^{-1}$ and 1200 $cm^{-1}$ in the double-passed receiver stream output. Although absorption bands of creatinine (FIG. 4e) are not clearly evident in these spectra, its enrichment is implied by the general enhancement of other low molecular weight constituents. This enrichment is further revealed by normalizing each spectrum to the KSCN absorption band (FIG. 6). The protein/$SCN^-$ ratio (a measure of the ratio of high/low MW constituents), may be gauged by the intensity of the protein amide I absorption at ~1650 $cm^{-1}$ in the normalized spectra. This ratio is increased for the sample stream output, and decreased for the receiver stream output as compared to the original sample. These observations confirm in turn that the receiver stream is relatively enriched in compounds of low molecular weight (e.g. creatinine), as desired.

While the aim of this study was to qualitatively assess LFDI as a preparatory step, some observations are relevant to the use in conjunction with quantitative IR spectroscopy. For example, if the method is to serve this purpose, the fractional extraction of any particular analyte must be independent of its absolute concentration. The KSCN-normalized pig urine spectra (FIG. 3) illustrate the independence of LFDI separation to absolute concentration; the relative concentration of KSCN and urea is essentially unchanged following the first and second passages despite the large variation in analyte absolute concentrations presented to the LFDI-card's sample reservoir. The same group of spectra further confirms that even following multiple passages, protein loss associated with protein-surface adsorption onto the LFDI-card [21] is not significant enough to impede detection. Finally, these spectra illustrate that although substantial chemical changes may occur through LFDI, spectral patterns for the analyte of interest may remain visually imperceptible. This does not rule out the possibility of quantitative analysis however, since multivariate analysis exploits subtle spectral signatures.

Along with the general merits of LFDI sample preconditioning (e.g. no external source of energy is required to drive the separation, there is no physical filter to clog or replace, the LFDI-cards are inexpensive to manufacture and disposable), a number of specific benefits make its integration with reagent-free IR spectroscopy attractive. Using a receiver fluid as simple as filtered water preserves the technique's reagent-free nature. There is no loss of potential diagnostic information since all of the original sample's constituents are retained within the two streams. Indeed, relative concentrations may be manipulated in such a way as to produce comparable absorption strengths (and hence permitting quantification) for constituents spanning a very wide concentration range. Finally, the use of LFDI separation to replace the centrifugation process has been demonstrated previously [15] the cellular content from whole blood samples being retained in the sample stream output. This suggests the clear possibility of point-of-care IR spectroscopic diagnostics. For example, independence from the prerequisite sample preparation step of whole blood centrifugation would yield both practical and financial benefits; its implementation to IR spectroscopy being achieved though a new set of PLS trails that use whole blood as the sample and a suitable receiver fluid, (e.g. PBS).

These qualitative experiments demonstrate that LFDI preconditioning of (bio)fluids has clear benefits for subsequent analytical IR spectroscopic analysis. In particular, LFDI preconditioning enhances the relative concentrations of relevant urine and serum analytes that cannot otherwise be quantified by IR spectroscopy, making their IR spectral contributions meaningful. The same sample preconditioning is equally pertinent to disease diagnosis based upon the classification of IR spectra. Here, rather than deriving analyte levels from IR spectrum, subtle spectral patterns are used to distinguish normal specimens from those corresponding to diseased patients [8-11]. Although LFDI sample preconditioning has been used previously in conjunction with mass spectroscopy, high performance liquid chromatography, fluorescence and magnetic resonance, there is no indication that the method has been considered of use as a preparative technique for IR spectroscopic analysis. This study therefore represents the first account of LFDI's applicability in enhancing the accuracy of IR spectroscopic clinical analysis and diagnostics.

Also demonstrated is the practice of dilution compensation and analyte concentration enhancement, by creating films of greater effective optical pathlength. To efficiently exploit this central characteristic of an integrated LFDI preconditioning and reagent-free IR technology it will be necessary to design LFDI-cards suitable for the purpose. Presently, no such LFDI-cards are commercially available, card designs typically being geared towards traditional (reagent) analytical methods and therefore, based upon criteria contrary to those we wish to exploit, (i.e. micro liter sample and output volumes to reduce the quantity of reagent necessary). Distinguishing characteristics of basic IR-specific LFDI-cards include i) an ability to accept sample volumes of between approximately 200 to 8000 µl, ii) redundancy of the receiver fluid input reservoir for active mode LFDI-cards (i.e. receiver fluids are pumped directly through the pump), and iii) the production of preconditioned output volumes of between approximately 200 to 8000 µl. Also the capability to automatically deposit the preconditioned output onto an appropriate IR substrate for dry film creation will be a key feature for point-of-care IR-specific cards. This anticipates the design of hybrid LFDI-cards, comprised of plastic and IR compatible substrates (e.g. silicon). Finally, more complex card designs are envisioned, the sample being taken from a single reservoir, divided and directed to pass through numerous LFDI-diffusion channels. The resultant preconditioned outputs are then either directed to further LFDI-channels (multiple passages) or discharged and dried onto IR substrates for IR spectral acquisition and analysis. In this manner, each of the final output streams is tuned for a specific MW range so that a large range of analytes may be measured from a single preconditioned sample, using either a single spectrum or a combination of spectra as the basis for each assay. Similarly, a range of IR spectra from various microfluidic output streams for a single sample may be combined and analyzed to enhance the accuracy of diagnostic applications.

Another logical development in the integration of LFDI preconditioning and reagent-free IR technologies is the goal of hardware integration, (i.e. a single system that incorporates the components and processes of: a pump system (for active mode cards), IR-specific LFDI-card, film creation, IR spectrometer and analysis of the resultant IR spectrum).

Practical issues that might hinder routine use of passive LFDI sample preconditioning in this application, including the need for multiple passes and subsequent high dilution, may be addressed by using pressure driven LFDI-cards. This technology typically incorporates an ultra low pulse pump system that enables researchers to optimize assays and precisely control fluid flow, at micro to pico volumes. Used in combination with LFDI pressure driven 'active' lab cards, it allows for the highly reproducible separation of analytes based upon differences in their diffusion coefficients. Although active and passive LFDI-cards share a common diffusion channel concept (i.e. creation of a virtual diffusion barrier) their design and operation differ significantly from one another. Active cards typically employ a 'pusher fluid' to drive both sample and receiver fluids through the microfluidic channels, with the volume diverted to the 'product' stream, (i.e. either the receiver or sample stream output depending upon desired molecular weight enhancement), also being under pump (vacuum) control. In this manner, the input pump's flow rates effectively determine the fraction of diffusion channel occupied by sample and receiver streams, while the product stream (output pump) flow rate acts as a variable gate, determining the diffusion barrier's height. A pilot study will demonstrate whether active LFDI sample preprocessing provides improved quantitative analysis of analytes that are otherwise difficult or impossible to quantify by IR spectroscopy, (e.g. serum creatinine). The specific question to be addressed is whether the spectra of LFDI preconditioned samples can provide analytical methods that are more accurate than the corresponding methods for the unprocessed samples. The essential elements of this study, and results therefrom, are outlined below.

Figure 7:
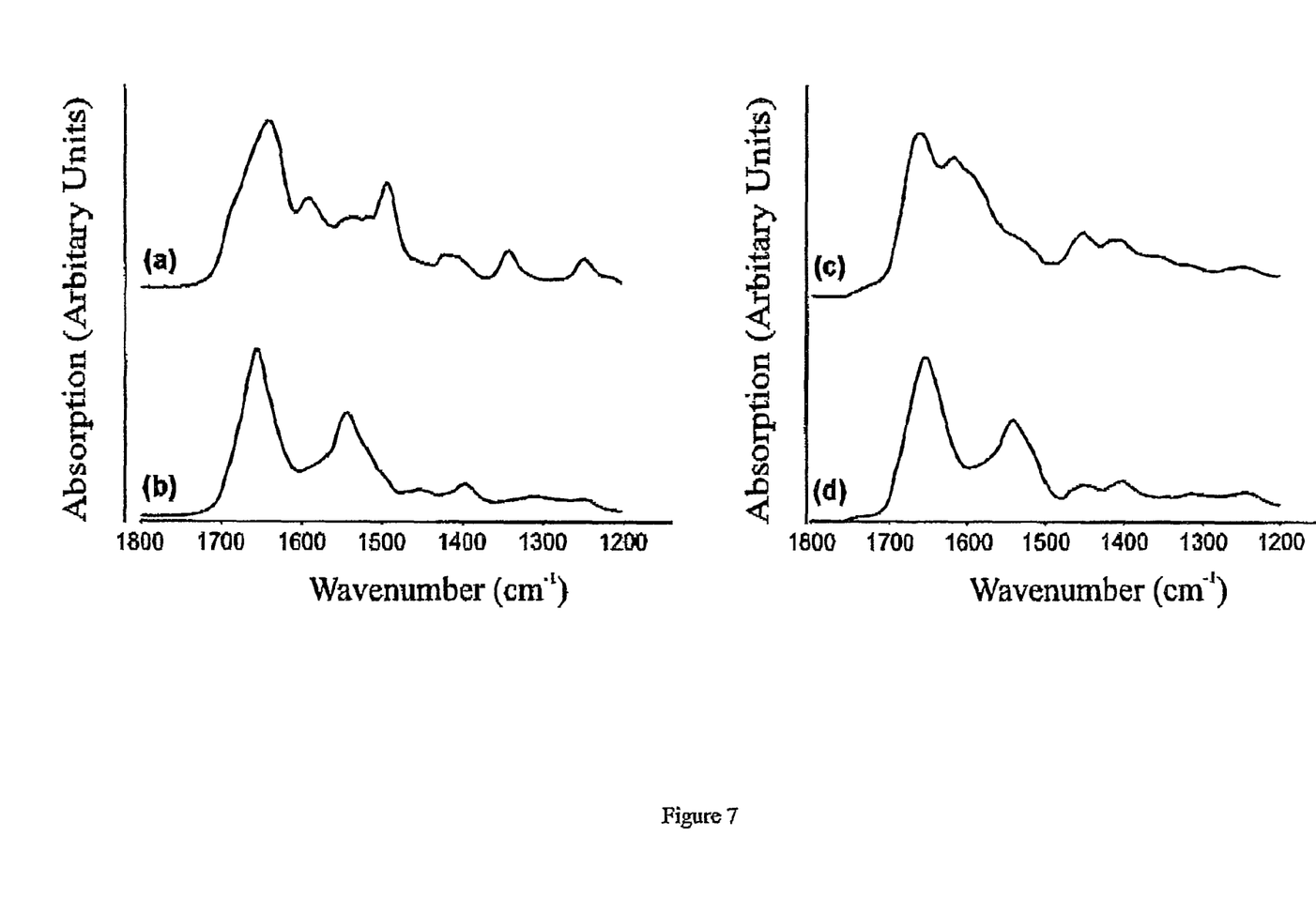
FIG. 7. IR absorption spectra of simulated serum (albumin at 50 g L$^{-1}$ and an elevated creatinine concentration of 4.2 mmol L$^{-1}$) demonstrating the emergence of creatinine related absorption features following active-LFDI preconditioning: (a) single pass receiver stream output, (b) original simulated sample; and IR absorption spectra of human serum at typical analyte levels: (c) single pass receiver stream output, (d) original human serum sample.
Figure 8:
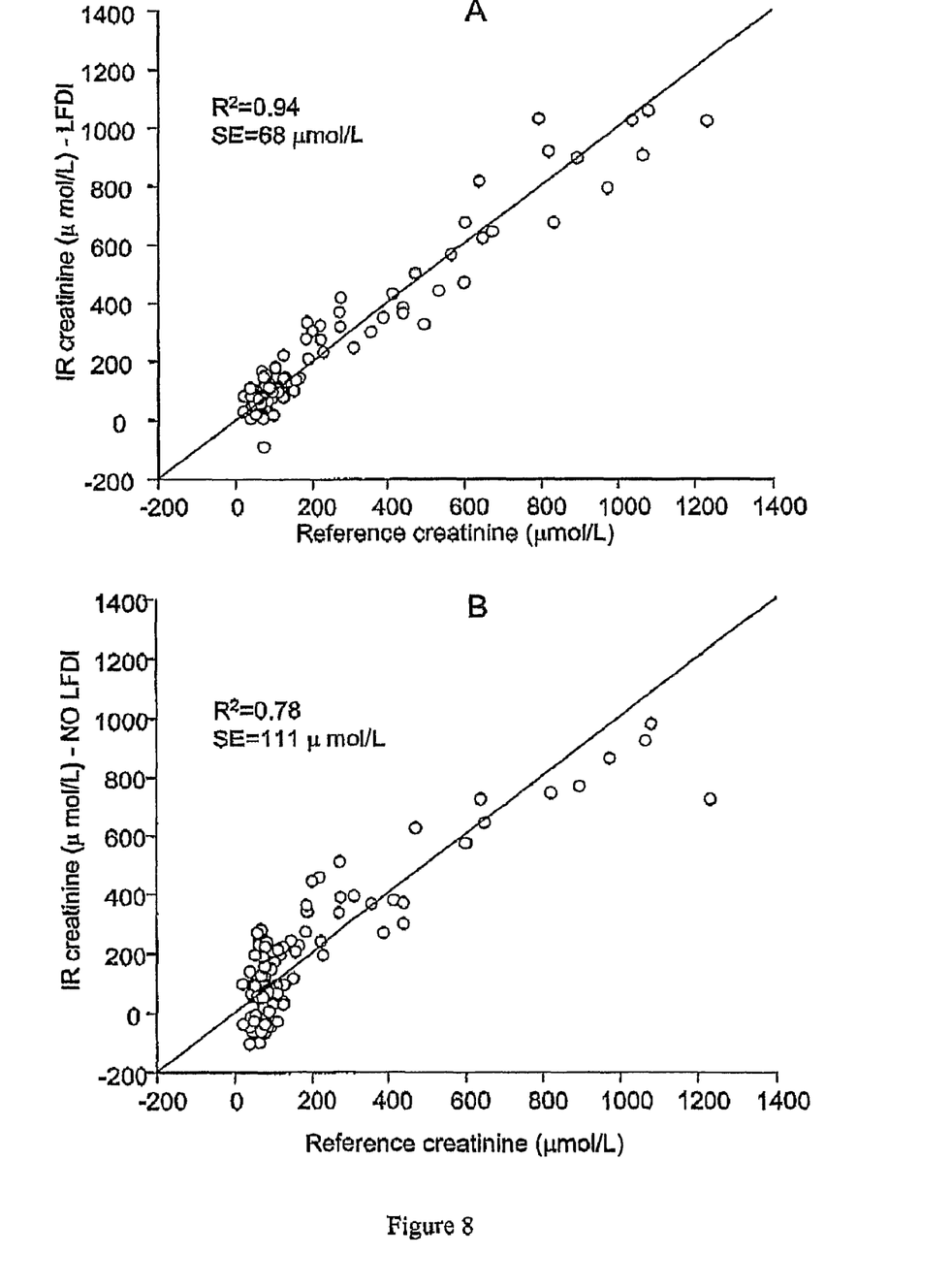
FIG. 8. Comparison of IR-derived creatinine levels as determined from the spectra of LFDI-preconditioned samples (A) and from spectra of unprocessed serum (B) to concentrations as determined by an accepted clinical laboratory method. The line of identity has been included for reference.

Human serum specimens (n=102) were selected randomly from routine laboratory samples and analyte levels provided by standard clinical chemistry assays (experimental protocol was approved by the Human Ethics Committee of the National Research Council of Canada). Active LFDI-cards (ActiveH™ Lab Card SMHF-01) were used in combination with their associated micro-pump platform (microFlow™ System, Micronics, Inc. Redmond, Wash., USA). Appropriate volumes of receiver fluid (here, KSCN solution at $2\,g\,L^{-1}$) and undiluted serum sample were introduced to the cards and the resultant receiver and sample stream outputs harvested. Films were prepared for the original serum samples by depositing and thoroughly drying a quantity of 4 µl onto circular silicon (Si) windows (approx. 4 mm diameter). Films of the LFDI receiver stream output were prepared by depositing a total volume of 50 µl (stacked in successive aliquots of 20 µl, 20 µl and 10 µl, each of which was allowed to dry before the next aliquot was added). IR absorption spectra (800-4000 $cm^{-1}$) were acquired for each dry film using a Bruker Vector 22 HTS-XT Fourier transform IR spectrometer, with a blank Si window used for the background measurement (256 scans were acquired at 4 $cm^{-1}$ resolution for both background and sample spectra). PLS calibration models that optimally relate spectral features to the reference analyte levels were developed using I) the entire set of spectra for the raw serum samples, and II) the corresponding set of spectra for LFDI-processed receiver streams. Simulated serum samples with albumin at approximately normal physiological level (50 g $L^{-1}$) and the target analyte creatinine at an elevated level (4.2 mmol $L^{-1}$), were also prepared and LFDI-processed in the manner described for qualitative analysis. Spectra of the LFDI-processed simulated and genuine serum samples illustrate that a substantial change in the relative concentration of relevant serum analytes is attainable with a single pass when using active-LFDI technology (FIG. 7). As with the previously described passive LFDI-card experiment though (FIG. 5), an explicit qualitative demonstration of creatinine's enrichment in genuine serum is improbable, since other constituents of comparable molecular weight will experience a similar concentration enrichment relative to protein. However, quantitative creatinine levels provided by PLS models using spectra for the LFDI preconditioned samples (FIG. 8), show substantial improvement over their analogous non-LFDI samples. Results indicate that following LFDI preconditioning there is an increase of approximately 20% between their $R^2$ values, (i.e. better correlation between creatinine related IR absorption features and serum creatinine concentrations) and a 70% decrease between their SE values, (i.e. better accuracy). Specifically, $R^2=0.78$ and SE=111 µmol/L for non-LFDI samples; while $R^2=0.94$ (r=0.97) and SE=68 µmol/L for LFDI samples. This observation provides indisputable proof that the absorption spectrum of creatinine is more strongly represented in the spectra of the LFDI-processed samples than is the case for unprocessed serum. Finally, it is worth noting that further improvements to these preliminary quantitative results may prove possible by further refining the PLS model. Moreover, the design and subsequent operational parameters of the active LFDI-cards used here were far from optimal for our purpose. It is therefore strongly anticipated that the use of IR-specific LFDI-cards will significantly lower the detection threshold.

While the preferred embodiments of the invention have been described above, it will be recognized and understood that various modifications may be made therein, and the appended claims are intended to cover all such modifications which may fall within the spirit and scope of the invention.

REFERENCES

1. Shaw R A and Mantsch H H, "Infrared Spectroscopy in Clinical and Diagnostic Analysis", *Encyclopedia of Analytical Chemistry*, pp. 83-102, 2000
2. Shaw R A, Low Ying S, Man A and Liu K Z, "Reagent-free clinical analysis and diagnostics: Laboratory medicine in a new light", In Vitro *Diagnositic Technology*, 9, No. 9, pp. 43-49, 2003
3. Liu K Z, Shaw R A, Man A, Dembinski T C and Mantsch H H, "Reagent-free, simultaneous determination of serum cholesterol in HDL and LDL by infrared spectroscopy", *Clinical Chemistry*, 48, No. 3, pp. 499-506, 2002
4. Shaw R A, Low-Ying S, Leroux M and Mantsch H H, "Toward Reagent-free Clinical Analysis: Quantitation of Urine Urea, Creatinine, and Total Protein from the Mid-Infrared Spectra of Dried Urine Films", *Clinical Chemistry*, 46, No. 9, pp. 1493-1495, 2000
5. Shaw R A, Kotowich S, Leroux M and Mantsch H H, "Multianalyte Serum Analysis Using Mid-infrared Spectroscopy", *Annals of Clinical Biochemistry*, 35, pp. 624-632, 1998
6. Budinova G, Salva J and Volka K, "Application of Molecular Spectroscopy in the Mid-infrared Region to the Determination of Glucose and Cholesterol in Whole Blood and in Blood Serum", *Clinical Chemistry*, 51, No. 5, pp. 631-635, 1997
7. Rohleder D, Kiefer W and Petrich W, "Quantitative analysis of serum and serum ultrafiltrate by means of Raman spectroscopy", *Analyst*, 129, pp. 906-911, 2004
8. Shaw R A, Kotowich S, Eysel H H, Jackson M, Thomson G T D and Mantsch H H, "Arthritis Diagnosis Based upon the Near-infrared Spectrum of Synovial Fluid", *Rheumatology International*, 15, pp. 159-165, 1995
9. Staib A, Dolenko B, Fink D J, Fruh J, Nikulin A E, Otto M, Pessin Minsley M S, Quarder O, Somorjai R, Thienel U, Werner G and Petrich W, "Disease pattern recognition testing for rheumatoid arthritis using infrared spectra of human serum", *Clinica Chemica Acta*, 308, No. 1-2, pp. 79-89, 2001
10. Petrich W, Dolenko B, Frh J, Ganz M, Greger H, Jacob S, Keller F, Nikulin A E, Otto M, Quarder O, Somorjai R L, Staib A, Werner G and Wielinger H, "Disease Pattern Recognition in Infrared Spectra of Human Sera with Diabetes Mellitus as an Example", *Clinical Chemistry*, 39, No. 19, pp. 3372-3379, 2000
11. Martin T C, Moecks J, Belooussov A, Cawthraw S, Dolenko B, Eiden M, von Frese J, Kohler W, Schmitt J, Somorjai R, Udelhoven T, Verzakov S and Petrich W, "Classification if signitures of Bovine Spongiform Encephalopathy in serum using infrared spectroscopy", *Analyst*, 129, pp. 897-901, 2004
12. Weigl B H and Bardell R L, "Microfluidics for Clinical Diagnostics-Promise and Current Reality", *Laboratory Medicine*, 35, No. 4, pp. 233-237, 2004
13. Weigl B H, Bardell R L and Cabrera C R, "Lab-on-a-chip for drug development", *Advanced Drug Delivery Reviews*, 55, pp. 349-377, 2003
14. Lion N, Rohner T C, Dayon L, Arnaud I L, Damoc E, Youhnovski N, Wu Z Y, Roussel C, Josserand J, Jensen H, Rossier J S, Przybylski M and Girault H H, "Microfluidic systems in Proteomics", *Electrophoresis*, 24, pp. 3533-3562, 2003
15. Jandik P, Weigl B H, Kessler N, Cheng J, Morris C J, Schulte T adn Avdalovic N, "Initial Study of Using a Laminar Fluid Diffusion Interface for Sample Preparation in High-Performance Liquid Chromatography", *Journal of Chromatography A*, 954, pp. 33-40, 2002
16. Weigl B H and Hedine K, "Lab-on-chip-based separation and detection technology for clinical diagnostics", *American Clinical Laboratory*, 21, No. 2, pp. 8-13, 2002
17. Schulte T H, Bardell R L and Weigl B H, "Microfluidic Technologies in Clinical Diagnostics", *Clinica Chemica Acta*, 321, pp. 1-10, 2002
18. Weigl B H, Bardell R L, Kesler N and Morris C J, "Lab-on-Chip Sample Preparation Using Laminar Fluid Diffusion Interfaces-Computational Fluid Dynamics Model Results and Fluidic Verification Experiements", *Fresenius Journal of Analytical Chemistry*, 371, No. 2, pp. 97-105, 2001
19. Kamholz A E and Yager P, "Theoretical Analysis of Molecular Diffusion in Pressure-Driven Laminar Flow in Microfluidic Channels", *Biophysical Journal*, 80, pp. 155-160, 2001
20. Weigl B H, Bardell R, Schulte T and William C, "Passive Microfluidic-Ultra-Low-Cost Plastic Disposable Lab-on-a-Chips", *Proceedings of the 4th International Symposium on Micro Total Analysis Systems*, pp. 299-302, 2000
21. Brody J P, Kamholz A E and Yager P, "Prominent Microscopic Effects in Microfrabricated Fluidic Analysis Systems", Society of *Photo-optical Instrumentation Engineers*, 2978, pp. 103-110, 1998
22. Yager P, Bell D, Brody J P, Qin D, Cabrera C, Kamholz A and Weigl B, "Applying Microfluidic Chemical Analytical Systems to Imperfect Samples", *Proceedings of International Symposium on Micro Total Analysis Systems*, pp. 207-212, 1998
23. Weigl B H and Yager P, "Silicon-Microfabricated Diffusion-Based Optical Chemical Sensor", *Sensors and Actuators B*, 38, pp. 452-457, 1997
24. Brody J P and Yager P, "Diffusion-Based Extraction in a Microfabricated Device", *Sensors and Actuators A*, 58, pp. 13-18, 1997
25. Holl M R, Galambos P, Forster F K, Brody J P Afromowitz M A and Yager P, "Optimal Design of a Microfabricated Diffusion Based Extraction System", Proceedings of 1996 ASME Meeting ASME DSC59, 189-195, 1996
26. Brody J P, Yager P, Goldstein R E and Austin R H, "Biotechnology at Low Reynolds Numbers", *Biophysical Journal*, 71, No. 6, pp. 3430-3441, 1996
27. Burtis C A and Ashwood E R (eds.), "Appendix" in *Tietz Fundamentals of Clinical Chemistry*, WB Saunders, Philadelphia, 1996

The invention claimed is:
1. A method of analyzing a multi-constituent fluid sample comprising:
   a) providing a multi-constituent fluid sample in which infrared absorption features of low concentration ana- lytes are masked by infrared absorption features of relatively high concentration analytes, or lie below the threshold of detection;

b) placing a stream of the fluid sample in laminar flow contact with a receiver stream under conditions in which inertial effects are negligible using a microfluidic laminar fluid diffusion interface device such that diffusion occurs between the sample stream and the receiver stream, which form a sample stream output, which undergoes relative concentration enrichment in relatively high molecular weight analytes and a receiver stream output, which undergoes relative concentration enrichment in relatively low molecular weight analytes, said receiver stream including an internal standard having a unique absorption peak within the spectral window of approximately 2000-2600 $cm^{-1}$;

c) collecting the sample stream output and the receiver stream output from the device;

d) depositing individually the sample stream output and/or the receiver stream output onto an infrared compatible substrate and drying to a film, and;

e) measuring the infrared spectrum for the film dried from the sample stream output and/or the film dried from the receiver stream.

2. The method according to claim 1 wherein prior to step (e) successive aliquots of the sample or receiver stream output are applied and dried sequentially to produce a film of greater effective optical pathlength.

3. The method according to claim 1 wherein step (b) is repeated at least once prior to step (c), substituting either the sample stream output or receiver stream output for the original fluid sample under investigation, thereby bringing about further relative concentration enrichment in either high molecular weight analytes or low molecular weight analytes.

4. The method according to claim 1 wherein the infrared spectrum is further subject to a spectral pattern recognition procedure.

5. The method according to claim 1 wherein the fluid sample is serum, the high concentration analyte is albumin and the low concentration analyte is creatinine.

6. The method according to claim 1 wherein the fluid sample is urine, the high concentration analytes are urea and creatinine, and the low concentrate analyte is protein.

7. The method according to claim 1 wherein the internal standard is selected from the group consisting of potassium thiocyanate (KSCN), ferricyanide, thiocynates, isocynates and azides.

8. The method according to claim 1 wherein the internal standard is potassium thiocyanate (KSCN).

9. The method according to claim 1 wherein the spectrum is normalized to the internal standard band intensity.

10. The method according to claim 1 wherein the spectrum is normalized to the KSCN band intensity.

* * * * *